US00PP30491P3

(12) United States Plant Patent
Hancock

(10) Patent No.: US PP30,491 P3
(45) Date of Patent: May 14, 2019

(54) STRAWBERRY PLANT NAMED 'REDSTART'

(50) Latin Name: ***Fragaria* x *ananassa***
Varietal Denomination: Redstart

(71) Applicant: Board of Trustees of Michigan State University, East Lansing, MI (US)

(72) Inventor: James Hancock, Scarborough, ME (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 15/530,811

(22) Filed: Mar. 3, 2017

(65) Prior Publication Data

US 2018/0255673 P1 Sep. 6, 2018

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209
See application file for complete search history.

(56) References Cited

PUBLICATIONS

"MSU Releases New Strawberries: Redstart & Wasatch", posted on Dec. 27, 2016; http://www.technologies.msu.edu/msu-releases-new-strawberries-redstart-wasatch, accessed on Jul. 18, 2017.
"Redstart Day-Neutral Strawberry—MSU 67"; http://msut.technologypublisher.com/technology/22786, accessed on Jul. 18, 2017.

*Primary Examiner* — Keith O. Robinson
(74) *Attorney, Agent, or Firm* — McKee, Voorhees & Sease, PLC

(57) ABSTRACT

A new and distinct *Fragaria* x *ananassa* plant named 'Redstart', particularly characterized as a weak day-neutral long fruiting variety.

2 Drawing Sheets

Botanical name of the genus and species of the plant claimed: The strawberry cultivar of this invention is botanically identified as *Fragaria* x *ananassa*.

Variety denomination: The variety denomination is 'Redstart'.

BACKGROUND OF THE INVENTION

The present invention relates to a new and distinct variety of a strawberry plant, botanically known as *Fragaria* x *ananassa* of the Rosaceae family, and hereinafter referred to by the variety denomination 'Redstart'.

The new *Fragaria* x *ananassa* variety is a product of a planned breeding program conducted by the inventors. The objective of the breeding program was to develop a new *Fragaria* x *ananassa* variety intended for the Midwestern and Northeastern USA, Ontario, and Quebec and the Pacific Northwest. It is a weak day-neutral, and has a long fruiting season.

The new variety originated from a cross between female parent 'Honeoye' (unpatented) and male parent 'Chandler' (U.S. Plant Pat. No. 5,262) made in a greenhouse at Michigan State University East Lansing, Mich. in March 2006. 'Redstart' was first selected in the summer of 2007 from a family of 76 planted in an open filed in Benton Harbor, Mich. It was re-evaluated in the same field the following spring and was then designated as MSU 67.

Asexual propagation of the new *Fragaria* x *ananassa* variety by runners was first performed at Michigan State University East Lansing Mich. in the fall of 2008, where runners from the original mother plant were dug up and transferred to a greenhouse at Michigan State. The potted plants were allowed to runner in the summer of 2011 and 2013 and the resulting daughter plants were rooted in sterilized soil. These plants were encouraged to go dormant each winter by leaving the greenhouse unheated.

Horticultural examination has demonstrated that the combination of characteristics as herein disclosed for the new variety was firmly fixed and retained through successive generations of asexual propagation. The new variety propagates true-to-type.

BRIEF DESCRIPTION OF THE INVENTION

The following traits have been repeatedly observed and are determined to be characteristics of 'Redstart', which in combination, distinguish this strawberry plant as a new, unique and distinct variety. 'Redstart' is a vigorous weak day-neutral variety, with high yields and excellent fruit quality.

In comparison to the parental varieties, 'Honeoye' and 'Chandler' (U.S. Plant Pat. No. 5,262), 'Redstart' differs primarily in the traits listed in Table 1.

TABLE 1

Comparison with parent varieties

| Trait | Female Parent 'Honeoye' | Male Parent 'Chandler' | Redstart' |
|---|---|---|---|
| Fruiting season | Short-day | Short-day | Day-neutral |
| Plant vigor | High | Medium | High |

TABLE 1-continued

| Comparison with parent varieties | | | |
|---|---|---|---|
| Trait | Female Parent 'Honeoye' | Male Parent 'Chandler' | Redstart' |
| Fruit shape | Conic | Long conic | Conic |
| Fruit color | Dark red | Medium red | Medium red |

Of the many commercial varieties known to the present inventors, the most similar in comparison to the new *Fragaria* x *ananassa* 'Redstart' is *Fragaria* x *ananassa* 'Albion', (U.S. Plant Pat. No. 16,228) or 'Seascape' (U.S. Plant Pat. No. 7,614). 'Redstart' proved to be more vigorous, had higher yields and better fruit color than 'Albion', although it was smaller fruited and less firm. Their fruit flavor was comparable. 'Redstart' had higher vigor and yields than 'Seascape', better tasting fruit and comparable firmness. Its fruit were paler than 'Seascape'. 'Redstart' did not display any symptoms of common diseases in the field trials. Description of field trials is below.

Trials

Ten plants of MSU 67 were planted in 2012 and 2014 with other MSU selections in an open field in Benton Harbor, Mich. and in Burlington, Wash. under high tunnels. Plants were maintained on a black plastic mulch in raised beds at in Burlington, Wash., while in Benton Harbor, Mich. they were grown on flat beds without mulch. All flowers were removed from the first flush of blooms in the planting year. Adjacent to these trials were other plantings of the day-neutral cultivars 'Albion' (U.S. Plant Pat. No. 16,228) and 'Seascape' (U.S. Plant Pat. No. 7,614). The plants set in 2012 were evaluated in years one and two for weeks of fruiting, vigor, fruit size, productivity and fruit quality. The plants set in 2014 were evaluated for the same parameters in just that year.

Results

Michigan Field Trials (2012-2013)

In the open fields in Michigan in 2012 and 2013, 'Redstart' was acceptable to superior for all the rated characteristics (Table 2). It fruited for 6 weeks in 2012 and 5 weeks in 2013. In the first fruiting season (Table 2), 'Redstart' was more vigorous than 'Albion' and had better fruit color. It had similar yields, fruit appearance and flavor, but its fruit were smaller and softer. 'Redstart' out-yielded 'Seascape' and was better flavored, had comparable fruit size and appearance, but had a little less internal fruit color and was slightly softer.

In the second fruiting season, 'Redstart' had much higher vigor and yields than 'Albion', and had comparable fruit appearance, color and flavor. Its fruit were not as firm and were smaller. 'Redstart' was more vigorous than 'Seascape' and had larger, more attractive fruit with better flavor. It had lower yields than 'Seascape' and was less colored.

TABLE 2

Strawberry trials in the open field in Benton Harbor, MI in 2012 and 2013.

| | | Cultivars | | |
|---|---|---|---|---|
| Year | Characteristic | 'Albion' | Redstart' | 'Seascape' |
| 2012 | Plant vigor | 7[a] | 8 | 8 |
| | Total Yield | 9 | 9 | 7 |
| | Fruit size | 9 | 7 | 7 |
| | Fruit appearance | 8 | 8 | 8.5 |
| | External color | 6 | 7 | 8 |
| | Internal color | 7 | 8 | 8 |
| | Firmness | 9 | 7 | 8 |
| | Flavor | 8 | 8 | 6 |
| 2013 | Plant vigor | 4 | 8 | 6 |
| | Total Yield | 3 | 6 | 7 |
| | Fruit size | 7 | 6 | 3 |
| | Fruit appearance | 8 | 8 | 7 |
| | External color | 7 | 8 | 9 |
| | Internal color | 7 | 8 | 8 |
| | Firmness | 10 | 8 | 8 |
| | Flavor | 7 | 7 | 6 |

[a]1 = poor; 7 = commercially acceptable, 10 = excellent

Washington Tunnel Trials (2012-2013)

In the tunnel trials in Washington in 2012 and 2013 (Table 3), 'Redstart' was acceptable to superior for all the rated characteristics, except fruit size in 2013. It fruited for 11 weeks in 2012 and 13 weeks in 2013.

In the first fruiting season under the hoops in Mt. Vernon, 'Redstart' had higher vigor and yields than 'Albion', but was less firm and not quite as flavorful. They had comparable color and appearance. 'Redstart' was more vigorous than 'Seascape', had larger fruit and was more flavorful. The fruit of 'Seascape' had less color than 'Redstart' and was slightly less firm.

In the second harvest season, 'Redstart' was much more vigorous than 'Albion' and had better color. 'Albion' was larger fruited and more firm, and they were comparable in yield. 'Redstart' had more vigor than 'Seascape' and had slightly lower yields and fruit weight. They were comparable in fruit color, firmness and flavor.

TABLE 3

Strawberry trials in hoop houses in Mt. Vernon, WA in 2012 and 2013.

| | | Cultivar | | |
|---|---|---|---|---|
| Year | Characteristic | 'Albion' | Redstart' | 'Seascape' |
| 2012 | Plant vigor | 7[a] | 8 | 7 |
| | Total Yield | 8 | 9 | 9 |
| | Fruit size | 9 | 8 | 7 |
| | Fruit appearance | 8 | 8 | 8 |
| | External color | 8 | 8 | 9 |
| | Internal color | 6 | 6 | 8 |
| | Firmness | 10 | 8 | 9 |
| | Flavor | 8 | 7 | 6 |
| 2013 | Plant vigor | 8 | 10 | 8 |
| | Total Yield | 8 | 8 | 9 |
| | Fruit size | 10 | 6 | 7 |
| | Fruit appearance | 8 | 7 | 8 |
| | External color | 8 | 8 | 8.5 |
| | Internal color | 6 | 8 | 8 |
| | Firmness | 10 | 8 | 8 |
| | Flavor | 9 | 8 | 8 |

[a]1 = poor, 7 = commercially acceptable, 10 = excellent

Michigan Field Trials and Washington Tunnel Trials in 2014

In both Michigan and Washington in 2014, all characteristics of 'Redstart' were rated acceptable to superior. In Michigan, 'Redstart' fruit were smaller than 'Albion' and less firm, but they had better color and their plants had higher vigor and yields; 'Redstart' and 'Albion' were comparable in flavor and fruit appearance. In Washington, 'Redstart' fruit were less firm and smaller than 'Albion', but they had better appearance and internal color, and the plants had higher yields.

TABLE 4

Strawberry trials in the open field in Mt. Vernon, WA and in Benton Harbor, MI in 2014.

| | | Cultivar | |
|---|---|---|---|
| Location | Characteristic | 'Albion' | Redstart' |
| MI | Plant vigor | 7[a] | 8 |
| | Total Yield | 7 | 8 |
| | Fruit size | 8 | 7 |
| | Fruit appearance | 8 | 8 |
| | External color | 6 | 8 |
| | Internal color | 7 | 7 |
| | Firmness | 9 | 7 |
| | Flavor | 8 | 8 |
| WA | Plant vigor | 8 | 7 |
| | Total Yield | 7 | 8 |
| | Fruit size | 8 | 7 |
| | Fruit appearance | 7 | 8 |
| | External color | 9 | 7 |
| | Internal color | 7 | 8 |
| | Firmness | 9 | 7 |
| | Flavor | 8 | 8 |

[a]1 = poor; 7 = commercially acceptable, 10 = excellent

BRIEF DESCRIPTION OF THE PHOTOGRAPHS

The accompanying photographs illustrate the overall appearance of the new *Fragaria* x *ananassa* variety 'Redstart' showing the colors as true as is reasonably possible with colored reproductions of this type. Colors in the photographs may differ slightly from the color values cited in the detailed morphological description, which accurately describe the color of 'Redstart'. Plants were set in the field in April and the photographs taken in June.

FIG. 1 shows a close up of a typical fruit bearing plant of 'Redstart' with flowers.

FIG. 2 shows a typical row of 'Redstart' planted in black plastic mulch.

DETAILED BOTANICAL DESCRIPTION

The new *Fragaria* x *ananassa* 'Redstart' has not been observed under all possible environmental conditions. The phenotype of the new variety may vary with variations in environment such as temperature, light intensity, day length or soil without any change in the genotype of the strawberry plant.

The aforementioned photographs, together with the following observations, measurements and values describe plants of 'Redstart' as grown in the field in Benton Harbor, Mich., under conditions which closely approximate those generally used in commercial practice. The described plants were propagated from stolons and planted at a distance of 25 cm in sandy red loam soil at an elevation of about 30 meters above sea level, with drip irrigation and fertilizers as generally used in commercial practice. Average annual precipitation is about 550 mm, with an average 350 mm of precipitation in winter (December to February). Mean diurnal minimum temperature in January is −8° C., and mean diurnal maximum temperature in July is 24° C.

Mother plants were planted in the beginning of May, in the field nursery at 2.5 m×2.5 m distance. Overhead irrigation with addition of fertilizers was used. The average day/night temperatures during the establishment of the daughter plants, between June to August, are 32° C./18° C., respectively. Runners appeared from June, which produce young daughter plants up till mid-September Unless otherwise stated, the detailed morphological description includes observations, measurements and values taken from May to June, 2014 and based on 'Redstart' plants grown in a greenhouse at Michigan State University. Quantified measurements are expressed as an average or a range of measurements taken from a number of plants of 'Redstart'. The measurements of any individual plant or any group of plants, of the new variety may vary from the stated average or range.

Color references are made to The Royal Horticultural Society Colour Chart (R.H.S.), (1986 edition), except where general colors of ordinary significance are used. All of the plants of 'Redstart', insofar as they have been observed, have been consistent in all the characteristics described below.

TABLE OF CHARACTERISTICS

Classification:

*Botanical.*—*Fragaria* x *ananassa.*

Parentage:

*Female or seed parent.*—'Honeoye' (Unpatented).

*Male or pollen parent.*—'Chandler' (U.S. Plant Pat. No. 5,262).

Propagation: By runners in a greenhouse at Michigan State University

Foliar characteristics in mid-summer:

*Plant height* (*mm*).—18.4 (14-23).

*Plant spread* (*mm*).—29.2 (25-31).

*Growth habit.*—Upright.

*Color.*—141B.

*Leaf division.*—Three leaflets.

*Mid-tier leaflet length* (*mm*).—73.2 (60-81).

*Shape* (*length/width*).—64.6 (62-73).

*Basal angle of terminal leaflet.*—10.2 (8-12).

*Serrations of terminal leaflet.*—24.6 (23-26).

*Serrations per leaf.*—73.8 (70-84).

*Petiolule length* (*mm*).—9.6 (6-11).

*Petiole length* (*mm*).—129.2 (108-138).

*Petiole diameter* (*mm*).—2.2 (2.0-2.5).

*Petiole color.*—145A.

*Venation.*—Pinnate.

*Leaf pubescence.*—None to sparse on lower surface.

*Leaf blistering.*—Absent.

*Leaf glossiness.*—Medium.

*Petiole pubescence.*—Sparse to moderate.

*Petiole pubescence direction.*—Perpendicular.

*Position of the inflorescence in relation to the foliage.*—Same level.

*Number of stolons.*—4-6.

Flowering and fruiting characteristics:

*Flowers per truss.*—6.1 (5-7).
*Flower position.*—Most exposed.
*Petal width (mm).*—10.5 (10-11.5).
*Petal color.*—White.
*Petal shape.*—Actinomorphic.
*Petal arrangement.*—Free.
*Calyx diameter (mm).*—23.2 (21-27).
*Corolla diameter (mm).*—28.2 (22-33).
*Size of the calyx in relation to the corolla.*—Smaller.
*Sepal length (mm).*—11.3 (10.5-14.5).
*Sepal width (mm).*—5.6 (4.5-7.0).
*Sepal color.*—147A.
*Stamens.*—Present.
*Number of stamens.*—10-15.
*Pedicle length (mm).*—18.9 (13-24.5).
*Pedicle diameter (mm).*—1.3 (1.1-2.0).
*Pedicle color.*—146D.
*Fruit width (mm).*—33.6 (31.5-35.50).
*Fruit length (mm).*—37.7 (35-40).
*Length/width.*—1.1 (1.0-1.3).
*Fruit shape.*—Conic to long conic.
*Firmness of the fruit.*—Firm.
*Size (g/frt).*—13.2 (10.2-14.8).
*Calyx diameter (mm).*—28.8 (24-35).
*Calyx position.*—Even with base of fruit.
*External color.*—45A.
*Internal color.*—45A.
*Depth of color.*—50%.
*Fruit per truss.*—6.1 (5-7).
*Achene color.*—163B (pale tan).
*Achene placement.*—Level.
*Time of beginning of flowering.*—Mid-April.

Fruit quality measurements:

*Soluble solids (%).*—8.2.
*Titratable acidity (%).*—9.2 (9.0-9.4).

The invention claimed is:

1. A new and distinct variety of *Fragaria* x *ananassa* plant named 'Redstart', as illustrated and described herein.

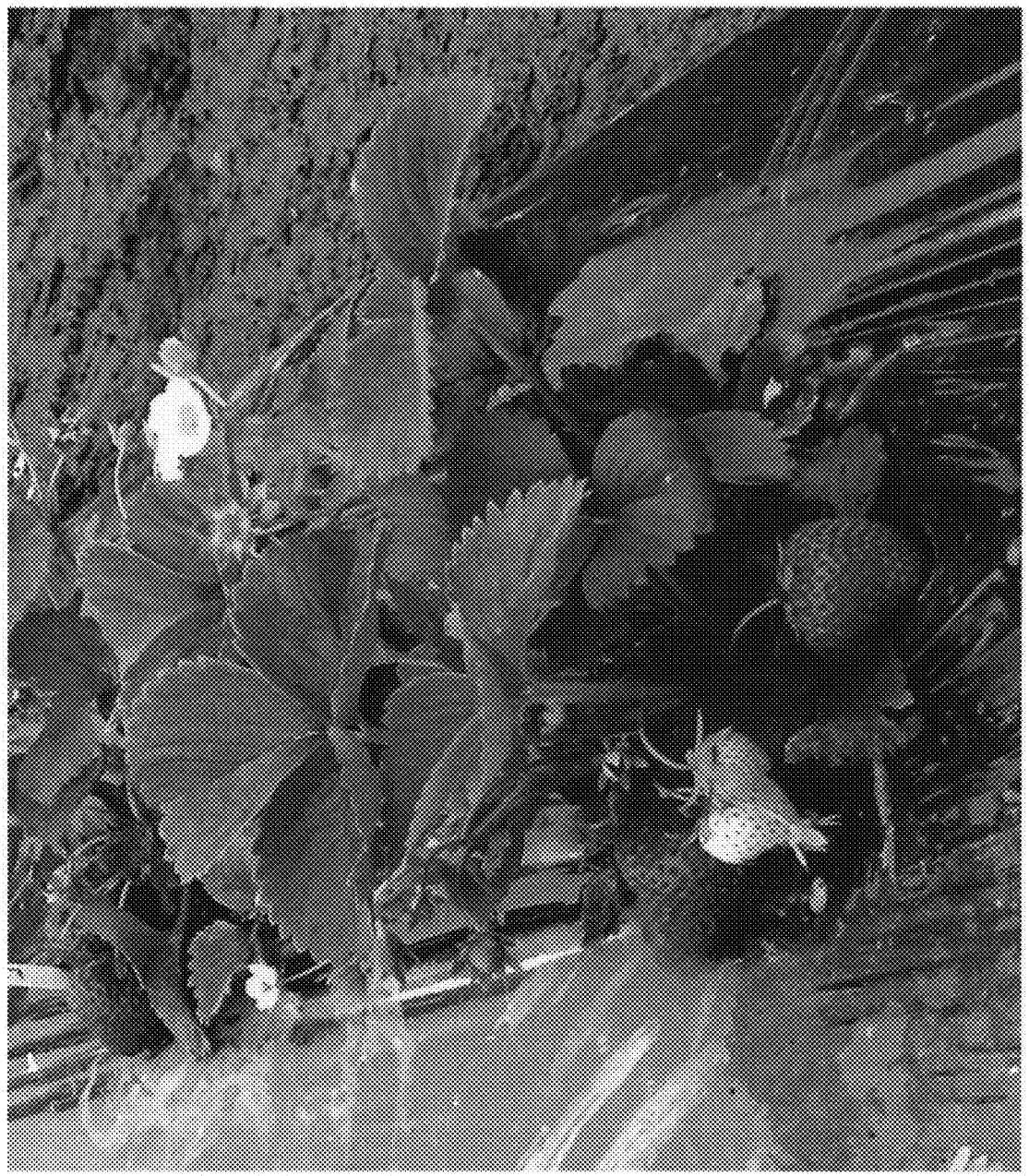

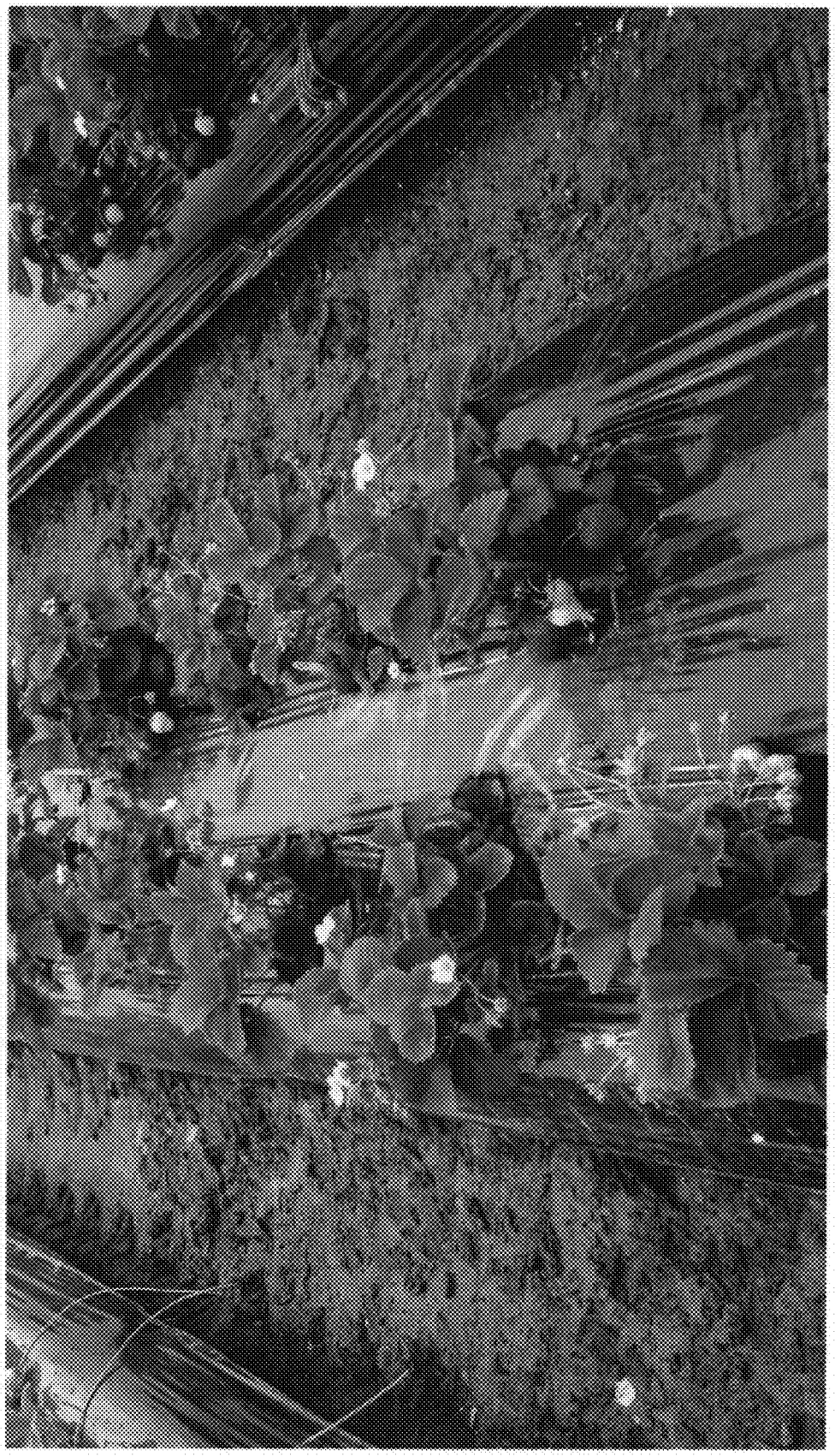

* * * * *